United States Patent [19]

Honeycutt

[11] Patent Number: 4,900,500

[45] Date of Patent: * Feb. 13, 1990

[54] POINT-OF-USE INFECTIOUS WASTE DISPOSAL SYSTEM

[75] Inventor: Travis W. Honeycutt, Irvine, Calif.

[73] Assignee: Isolyser Co., Inc., Norcross, Ga.

[*] Notice: The portion of the term of this patent subsequent to Mar. 28, 2006 has been disclaimed.

[21] Appl. No.: 329,827

[22] Filed: Mar. 28, 1989

Related U.S. Application Data

[63] Continuation-in-part of Ser. No. 4,593, Jan. 20, 1987, Pat. No. 4,816,307.

[51] Int. Cl.$^4$ .............................................. B65D 85/24
[52] U.S. Cl. ..................... 264/263; 206/366; 206/526; 264/267; 264/279.1; 428/2; 428/34.1; 428/35.7
[58] Field of Search ............ 156/298; 206/366, 524.5, 206/570, 571, 526; 220/1 T; 264/267, 279.1, 263; 428/34.1, 35.7, 2

[56] References Cited

U.S. PATENT DOCUMENTS

| | | | |
|---|---|---|---|
| 3,292,776 | 12/1966 | Penn | 206/366 X |
| 3,547,747 | 12/1970 | Roberts | 264/267 X |
| 3,638,709 | 2/1972 | Brown, Jr. et al. | 264/279.1 X |
| 3,653,567 | 4/1972 | Selvaggio | 206/570 X |
| 3,897,579 | 7/1975 | Weinstein | 428/179 X |
| 3,921,801 | 11/1975 | Sway | 206/575 |
| 3,999,653 | 12/1976 | Haigh et al. | 206/524.5 X |
| 4,134,929 | 1/1979 | Stoakley et al. | 525/305 X |
| 4,139,693 | 2/1979 | Schoenberg | 428/442 X |
| 4,170,585 | 10/1979 | Motegi et al. | 526/298 X |
| 4,171,416 | 10/1979 | Motegi et al. | 526/298 X |
| 4,320,157 | 3/1982 | von Hagens | 428/13 |
| 4,410,086 | 10/1983 | Simpson | 206/366 |
| 4,444,933 | 4/1984 | Columbus et al. | 525/295 X |
| 4,477,607 | 10/1984 | Litke | 525/295 X |
| 4,520,926 | 6/1985 | Nelson | 206/366 |
| 4,600,112 | 7/1986 | Shillington et al. | 206/366 X |
| 4,600,610 | 7/1986 | Hrovat et al. | 428/2 |
| 4,650,086 | 3/1987 | Morrison, Jr. | 206/524.5 X |
| 4,662,516 | 5/1987 | Baker, Sr. et al. | 206/366 X |
| 4,715,498 | 12/1987 | Hanifl | 206/366 |
| 4,722,472 | 2/1988 | Bruno | 206/366 |
| 4,759,445 | 7/1988 | McVay | 206/524.5 X |
| 4,816,307 | 3/1989 | Honeycutt | 428/34.1 |

OTHER PUBLICATIONS

Article: Infection Prevention Products Published in Biomedical Business International, vol. IX, No. 13, Jul. 10, 1986, pp. 128+129.

*Primary Examiner*—Henry F. Epstein
*Attorney, Agent, or Firm*—Limbach, Limbach & Sutton

[57] ABSTRACT

A method for containing potentially infectious devices. The potentially infectious devices are deposited in a container to which is added an oligomer or monomer-containing composition to at least partially envelope the potentially infectious devices. The oligomer or monomer-containing composition is caused to harden through polymerization or cross-linking of the oligomer or monomer to immobilize the devices, and to act as a sterilizing or disinfectant agent due in large part to the exothermic nature of the reaction.

20 Claims, No Drawings

POINT-OF-USE INFECTIOUS WASTE DISPOSAL SYSTEM

RELATED APPLICATIONS

The present application is a continuation-in-part of U.S. application Ser. No. 07/004,593, now U.S. Pat. No. 4,816,307, filed on Jan. 20, 1987, entitled "Novel Infectious Waste Containment".

TECHNICAL FIELD OF THE INVENTION

The present invention deals with infectious waste disposal systems and particularly those which are designed for use in hospitals and other environments in which medical practitioners routinely contaminate a host of devices such as needles, syringes, tubing and scalpels with blood and other bodily fluids which then require disposal.

BACKGROUND OF THE INVENTION

In hospitals, clinics and other environments in which ill patients are routinely examined and treated, medical practitioners contaminate a host of devices such as needles, syringes, tubing and scalpels with blood and other bodily fluids. This is often done when feeding patients, drawing bloods, vaccinating and otherwise inoculating patients against various diseases. Quite often, patients' bodily fluids are infected with pathogenic bacteria, viruses, fungi and other matter. The potential source of pathogenicity has been acute with the knowledge and identification of certain pathogens such as hepatitis B and the AIDS virus, among other deadly and infectious materials.

These pathogenetic materials are potentially a source of infection for doctors, nurses, aids, orderlies, technicians and even to visitors to the hospital or clinic, as well as to the patients themselves. The various devices infected must thus be contained and/or destroyed.

Currently, infectious waste, called "sharps", is generally disposed of by insertion of the infected material into a passive hard plastic container. These containers are then removed by housekeeping personnel and sent to a site for bagging and storage. After bagging, the containers are often stored or removed to yet another site for sterilization. Even when closed, locked and bagged, the containers are not airtight, and thus can potentially spill and contaminate the atmosphere. Handling of the waste containers often results in infected needles penetrating storage containers, thus providing a potentially dangerous condition for housekeeping personnel.

Following sterilization, the contaminated material is often removed to another location for incineration, storage or disposal in a landfill. Thereafter, the waste disposal containers resemble, and are often referred to, as "porcupines" because the often used plastic containers shrink around the needles and other devices when heated in an autoclave or similar device, resulting in needle exposure through the sidewalls of the containers. In this condition, the containers are indeed quite dangerous to handle, whether or not they remain the housing for infectious devices.

In addition to the above recited difficulties, current state of the art disposal techniques are further flawed in the use of so-called "anti-removal" or "anti-theft" containers. Infectious devices are often put into plastic containers which contain guards for preventing needle retrieval. However, it is relatively easy to reach into such containers and retrieve the "sharps". As such, current disposal methods do not render the needles and sharps irretrievable and unstable at the point of disposal.

One of the most serious deficiencies with current disposal methods is that they do not prevent the aerosoling or spilling of infectious materials into the ambient atmosphere, thus potentially causing the spread of infectious germs, bacteria, fungi and viral fragments. Current containers are not air-tight, even when they are eventually closed and locked. As such, there remains outstanding potential for cross infection by vectors such as flies, rodents, etc., and "odor" is a big problem.

It is thus an object of the present invention to provide a superior means for containing potential infectious devices which overcomes the difficulties recited above.

This and further objects of the present invention will be more fully appreciated when considering the following disclosure.

SUMMARY OF THE INVENTION

In its broadest sense, the present invention is a method for sterilizing and containing potentially infectious devices. The method comprises depositing the potentially infectious devices in a container to which is added a sufficient quantity of an acrylic monomer-containing composition which includes, for example, acrylates which are esters of acrylic acid and their derivatives, methacrylic acids and their derivatives, and acrylamides and their derivatives. The composition is to be added to a container to fully or at least partially envelope the potentially infectious devices. The acrylic monomer-containing composition is then hardened through polymerization of the aqueous acrylic monomer with a corresponding exotherm to immobilize and sterilize or at least neutralize the potentially infectious devices.

DETAILED DESCRIPTION OF THE INVENTION

The present method involves the entrapment, anchoring and fuming or precipitation of contaminated and/or infected "sharps" and their aerosol through the use of a container and solidifying agent at the point of disposal. The container is first filled by hospital personnel with the infected "sharps" material, and then filled with a liquid which turns into a solid block of plastic with associated fuming and surface coating within a short period after the liquid is pored over the "sharps" or infectious devices. The liquid and fume contains biocides and produces biocidal activity and sanitizing heat during the course of the reaction, which is decidedly exothermic. The preferred solidifying liquid is an acrylic based monomer-containing composition which includes acrylic acids and their derivatives, methacrylic acids and their derivatives, as well as acrylamides and their derivatives. These act as fumers and sanitants. The aqueous/acrylic monomer-containing composition incorporates the potentially infectious fluids into their polymer matrices as the polymerization proceeds. The acrylic acid complexes amino acids and proteins which are known constituents of blood and bodily fluids, thus immobilizing and containing these fluids. As such, acrylic and acrylic ester monomer-containing compositions provide an ideal material to contain potentially infectious devices which have been infected with bodily fluids. It is hypothesized that the monomer containing composition reacts through a polymerization cascade and causes a grafting reaction to take place whereby the organic matter in the infectious waste is thereby "caught up", bound or covalently reacted with the monomer and thus becomes a part of the "thermoset" matrix.

The preferred immobilizing composition comprises an acrylic or acrylate ester monomer having the following structure:

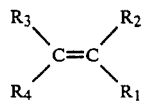

wherein:

$R_1$ is a member selected from the group consisting of —COOH and —COOR$_5$;

$R_2$ is a member selected from the group consisting of H,CH$_3$—, CH$_3$CH$_2$—, and CN—;

$R_3$ and $R_4$ are each a member selected from the group consisting of H, CH$_3$—, CH$_3$CH$_2$— and a halogen;

$R_5$ is a member selected from the group consisting of an alkyl of from 1 to 12 carbon atoms and preferably CH$_3$—, an alkoxyalkyl such as ethoxyethyl or hydroxyalkyl such as a hydroxyethyl, —CONH$_2$, an acrylamide and its bis product such as methylene-bis-acrylamide.

As an alternative, for example, the reaction product of a polyol and a diisocyanate can be employed as further described in Applicants' U.S. patent application Ser. No. 07/004,593 when stored hermetically away from moisture and air to engulf and encapsulate the "sharps". The reaction products of polyols and isocyanates produce oligomers when a molar excess of the diisocyanates are used. Subsequently, in the presence of a catalyst such as alkyl tin or mercury compounds or tertiary amines, for example, when water vapor or a liquid water is added to the oligomer, part of the excess isocyanate groups are converted to primary amines with the concurrent evolution of carbon dioxide. The primary amines thus produced then react with other isocyanate linkages to form crosslinks and a solid mass.

As acrylates polymerize via the free radical route, to enhance shelf life, it is preferable that a free radical scavenger be included in the composition. Such scavengers include hydroquinone, monoethyl ether of hydroquinone, butylated hydroxyanisole, butylated hydroxytoluene and t-butyl hydroquinone. Hydroquinone or its monoethyl ether is the preferred free radical scavenger for use herein. It is further contemplated that the monomer-containing compositions also include a "promoter", such as ferrous or cuprous salts, and in the case of "redox" catalyst systems, a reducing agent. These are materials such as sodium-meta-bisulfite, isoascorbic acid, sodium sulfite or tertiary amines such as N,N-dimethyl-toluedine or N,N-dihydroxyethyl-paratoluedine.

In the case of oligomers such as urethane prepolymers, such promoters are not necessary as ambient moisture combined with catalysts that are generally included with the prepolymers are all that is necessary to start the cross-linking or "hardening" reactions. The prepolymer, of course, must be kept away from moisture as it begins to harden on contact with moisture vapor.

It is further often useful that a plasticizer or solvent be employed in this composition and a product as simple as water may be particularly useful as a hazard free solvent. Plasticizers for use herein comprise one or members selected from the group consisting of monofunctional aliphatic esters, such as butyl acetate and butyl cyanoacetate, difunctional aliphatic esters, such as dibutyl phthalate, phosphate esters and phosphonate esters.

Also included as possible preferred expedients in the system are aldehydes such as formaldehyde and glutaraldehyde and phenols and its derivatives such as orthophenylphenol and its sodium salt as sterilants and/or disinfectants.

While an "oil" based or hydrophobic system is satisfactory, a more preferred system is one which is aqueous based. The aqueous base systems are preferred for land-fill considerations as aqueous based materials are easier to contain in a land-fill area due to various legal restrictions on burying "organic" materials.

The preferred viscosity of the present composition is that of water, approximately between 0 and 1000 cps when measured on a Brookfield viscometer at 20 rpms with a number 4 spindle. Although the composition can be thixotropic in nature, it is preferable not to employ a highly viscous material to insure that the monomer-containing or oligomer composition has the desirable "penetrating" effect to insure complete coverage over all utensils found within the container. If viscosity is to be increased, viscosity enhancers such as Cabosil ® PTG may be employed which is a hydrophobic fumed silica treated with polydimethylsiloxane. One could also employe PMMA, PECA and PEMA, as well as cellulose esters or polycarboxylic or polyacrylic acids for water based systems.

It is further contemplated that in practicing the present invention, an initiating agent or catalyst be employed to promote the polymerization of the monomer. Preferably, the catalyst consists of a persulfate, peroxide or perborate, alone, or in a solvent or plasticizer such as a detergent, soap or surfactant.

Catalysts can be deposited on the inside of the container or in a paper or sponge material which can be placed in the container to provide a concentration from approximately 0.001% to 5% of the effective volume of the container. A suitable solvent for the initiating agent can be water, while dioctylphthalate can be employed as a suitable plasticizer, or in the case of ammonium persulfate or sodium perborate tetrahydrate, it may be used as a dry powder.

EXAMPLE I

A 2 liter container that has been blow molded high density polyethylene was fitted with a screw lid. The inside of the container was coated with 4 grams of sodium perborate tetrahydrate. The container was filled with syringes and needles of the type used for intramuscular injection and venous blood withdrawal. After the container was filled with the syringes, there was sufficient void space for introduction of the immobilizing liquid to intermingle and fill the container. As such, the container was then filled to the bottle shoulder level with the solidifying composition which was composed of the following ingredients:

| | |
|---|---|
| Acrylic Acid | 40% (By Wt.) |
| Hydroxyethylmethacrylate | 7% |
| Methylene-bis-acrylamide | 2% |
| Isoascorbic acid | 1% |
| Deionized water | 50% |
| Hydroquinone | 300 ppm |
| Ferrous sulfate | 10 ppm |

As noted, the composition was inhibited with 300ppm of hydroquinone and ferrous sulfate was added to catalytically decompose the sodium perborate to hydrogen peroxide.

The container was then closed and turned upside down and shaken vigorously for 30 seconds. The container was allowed to sit on its side for 30 minutes to allow the solidifying liquid the opportunity to lock on the lid and decontaminate the finger guard area with fuming. As the monomers began to polymerize, heat was released from the exothermic reaction, causing a rise in temperature of the container and its contents to the range of approximately 150° to 200° F. As this occurred, a hard dense block of polyacrylates, acids and bisamides formed in the container which completely locked and anchored the infected syringes, and prevented their retrieval and/or use. Further, the heat of polymerization sanitized the container and formed a surface film in the voids. As the container began to cool down, it could be handled as ordinary sanitary trash.

EXAMPLE II

The process of Example I was repeated wherein the container housing the syringes further contained approximately 4 grams of benzoyl peroxide to which was added the following composition:

| Acrylic acid | 40% (by wt.) |
|---|---|
| Hydroxyethylmethylacrylate | 7% |
| Methylene-bis-acrylamide | 2% |
| N,N—dimethyl-para-toluidine | 0.5% |
| Deionized water | 50.5% |
| Hydroquinone | 300 ppm |

EXAMPLE III

A 250 gram, 4 liter HDPE container with a 63 mm mouth and cap was filled with 1050 grams of lubrisol's AMPS 2405A solution which is a 58% water solution of a sodium salt of a sulfonic acid derivative of acrylamide. To the container was then added approximately 14 grams of methylene-bis-acrylamide which served as a cross-linker or chain extender and 500 ppm orthophenylphenol. The container was then filled with infected syringes. After filling, the container was then topped off with water to fill the voids between the "sharps". To the container was then added 3.0 grams of ammonium persulfate, 1.5 grams of sodium sulfoxylate formaldehyde and 1.0 grams of a 5% FeSO4/95% Celite mixture. The container was capped and shaken well for 15 seconds. In 15 minutes, the container was solid, and there was a temperature rise of 20° F.

I claim:

1. In a method for containing potentially infectious devices comprising depositing the potentially infectious devices in a container, the improvement comprising adding to said container a sufficient quantity of a hardenable composition to at least partially envelop said potentially infectious devices, said hardenable composition comprising an acrylate monomer-containing liquid capable of polymerizing in an exothermic reaction to immobilize said potentially infectious devices.

2. The method of claim 1 wherein said acrylate monomer-containing composition is capable of at least partially sterilizing said potentially infectious devices upon the polymerization of said acrylate monomer.

3. The method of claim 1 wherein said acrylate monomer is a member selected from the group consisting of esters of acrylic acid, methacrylic acids and acrylamides and their derivatives.

4. The method of claim 1 wherein said acrylate monomer is of the following formula:

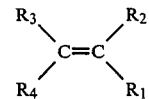

wherein:
R$_1$ is a member selected from the group consisting of —COOH and —COOR$_5$;
R$_2$ is a member selected from the group consisting of H, CH$_3$—, CH$_3$CH$_2$— and CN—;
R$_3$ and R$_4$ are each a member selected from the group consisting of H, CH$_3$—, CH$_3$CH$_2$— and a halogen;
R$_5$ is a member selected from the group consisting of an alkyl of from 1 to 12 carbon atoms, an alkoxyalkyl, —CONH$_2$, and acrylamide and its methylene bis product.

5. The method of claim 4 wherein R$_5$ is CH$_3$—.

6. The method of claim 4 wherein R$_5$ is a member selected from the group consisting of ethoxyethyl and hydroxyethyl.

7. The method of claim 1 wherein said hardenable composition further comprises a free radical scavenger.

8. The method of claim 7 wherein said free radical scavenger comprises a member selected from the group consisting of hydroquinone, monoethyl ether of hydroquinone, butylated hydroxyanisole, butylated hydroxytoluene and t-butyl hydroquinone.

9. The method of claim 1 wherein said hardenable composition further comprises a promoter.

10. The method of claim 9 wherein said promoter is a member selected from the group consisting of ferrous salts, cuprous salts, sodium-meta-bisulfite, isoascorbic acid and tertiary amines.

11. The method of claim 10 wherein said tertiary amines are N,N-dimethyl-toluidine or N,N-dihydroxyethyl-para-toluidine.

12. The method of claim 1 wherein said hardenable composition further comprises a solvent.

13. The method of claim 12 wherein said solvent is water.

14. The method of claim 1 wherein said hardenable composition further comprises a plasticizer.

15. The method of claim 14 wherein said plasticizer comprises a member selected from the group consisting of monofunctional aliphatic esters and difunctional aliphatic esters.

16. The method of claim 15 wherein said monofunctional aliphatic esters comprises butylacetate or butyl cyanoacetate.

17. The method of claim 15 wherein said difunctional aliphatic esters comprises dibutyl phthalate, phosphate esters or phosphonate esters.

18. The method of claim 1 wherein said hardenable composition has a viscosity of approximately between 0 and 1000 cps when measured on a Brookfield viscometer at 20 rpms with a number 4 spindle.

19. The method of claim 1 wherein said hardenable composition further comprises a catalyst.

20. The method of claim 19 wherein said catalyst comprises a member selected from the group consisting of a persulfate, peroxide and perborate.

* * * * *